United States Patent [19]

Magers et al.

[11] 4,147,514

[45] Apr. 3, 1979

[54] TEST MEANS AND METHOD FOR DETECTING KETONE BODIES

[75] Inventors: Thomas A. Magers, South Bend; David L. Tabb, Elkhart, both of Ind.

[73] Assignee: Miles Laboratories, Inc., Elkhart, Ind.

[21] Appl. No.: 853,390

[22] Filed: Nov. 21, 1977

[51] Int. Cl.² ............................................. G01N 33/16
[52] U.S. Cl. ................................. 23/230 B; 252/408; 422/56
[58] Field of Search ....................... 23/230 B, 253 TP; 252/408

[56] References Cited

U.S. PATENT DOCUMENTS

| | | | |
|---|---|---|---|
| 2,509,140 | 5/1950 | Free | 23/230 B X |
| 2,577,978 | 12/1951 | Nicholls et al. | 23/230 B X |
| 2,990,253 | 6/1961 | Smeby | 23/230 B X |
| 3,212,855 | 10/1965 | Rebar, Jr. et al. | 23/253 TP |
| 3,880,590 | 4/1975 | Ogawa et al. | 23/230 B X |

*Primary Examiner*—Morris O. Wolk
*Assistant Examiner*—Arnold Turk
*Attorney, Agent, or Firm*—Charles J. Herron

[57] ABSTRACT

Test means, method of making a test device and process for detection of ketone bodies are disclosed. More particularly, suitable test means are of the type having a nitroprusside in combination with at least one inorganic salt of a metal selected from the group of magnesium and calcium. Optionally, at least one primary amine is combined therewith. The compositions are advantageously incorporated with a carrier, such as a matrix or tablet, to provide a test device. The metal salt stabilizes the nitroprusside in solution at alkaline pH, allowing for a single-dip production method, promotes ionization of ketone bodies, resulting in a shortened reaction time, and stabilizes the resulting chromophoric complex. The chromophoric complex is further stabilized by the primary amine.

25 Claims, No Drawings

TEST MEANS AND METHOD FOR DETECTING KETONE BODIES

BACKGROUND OF THE INVENTION

The present invention relates generally to the field of diagnostic compositions, and more particularly, to diagnostic tests useful in qualitative and quantitative determination of ketone bodies in body fluids, especially acetoacetic acid in urine.

As used herein, ketone bodies includes compounds such as acetone, acetoacetic acid and β-hydroxybutyric acid (though the latter is not a ketone). The chemical relationship among these compounds is indicated below.

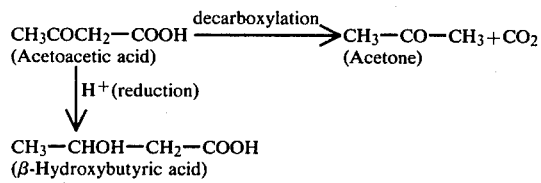

Acetone is a decomposition product of acetoacetic acid and is probably not otherwise produced as such in humans, although it is invariably found in urine when the other two compounds are present.

Acetoacetic and β-hydroxybutyric acids appear to be intermediate products in the breakdown of fatty acid chains (via acetoacetyl coenzyme A). Under normal conditions fatty acids are oxidized to carbon dioxide and water and intermediate products do not appear to any great extent in blood or urine.

When the body metabolizes inadequate amounts of carbohydrate because of metabolic disorder or inadequate diet, increased fatty acid metabolism gives rise to the appearance of ketone bodies in the blood (ketonemia) and urine (ketonuria). Clinical conditions, most especially diabetes mellitus, require detection and surveillance of ketonuria for management. Thus, efforts have been reported toward simplifying production and increasing stability of sodium nitroprusside tests which have been widely used for such detection.

The use of soluble nitroprussides in detection of ketone bodies, known as the Legal test, has long been recognized. Swinehart, *Coordination Chem. Rev.*, 2(4), 386–403 (December, 1967) presents a summary of the work concerning the reaction of sodium nitroprusside with acetone and acetoacetic acid. This work by Swinehart delineates the mechanism of reaction of sodium nitroprusside at the site of the acidic hydrogen as well as the action of the nitrosyl moiety of sodium nitroprusside.

Fortune U.S. Pat. No. 2,186,902 was among the first to disclose a formulation wherein the nitroprusside reaction is carried out in the presence of ammonia in order to develop particular colorations.

Free U.S. Pat. No. 2,509,140 later disclosed formulations for detection of ketone bodies in urine which contain water soluble nitroprusside, an aliphatic amino acid (glycine) and an alkaline material. Nicholls U.S. Pat. No. 2,577,978 discloses the addition of lactose or similar sugars to the Free composition.

Smeby U.S. Pat. No. 2,990,253 provides a test composition incorporated into a bibulous strip wherein, because of the instability of nitroprusside in an alkaline aqueous medium, the nitroprusside is kept separate. Separation is achieved by a two-step device preparation method wherein the nitroprusside is first applied to the carrier in an acid aqueous medium, thus preserving the stability of the compound, and, after drying, the carrier is dipped into a non-aqueous solution of organic bases such as various amines or amino alcohols to achieve the necessary alkalinity.

Mast U.S. Pat. No. 3,212,855 discloses an improved two-dip preparation wherein a bibulous carrier is first impregnated with an alkaline buffer and an amino acid and, after drying, is then impregnated with alkali metal nitroprusside, an organic film-forming compound of acid pH and an organic solvent.

Ogawa U.S. Pat. No. 3,880,590 discloses a ketone test strip prepared by a single-dip method. The composition is a nitroprusside salt in combination with a salt of a heavy metal of specific gravity more than 5, such as nickel, copper, cobalt, manganese, chromium and zinc, for determinations at acid pH. Other metals having a specific gravity greater than 5 include arsenic (5.7), lead (11.34) and mercury (13.6). Substances, such as buffers, used to keep the composition at alkaline pH are excluded.

Concern has been expressed about the use of ketone detection procedures involving heavy metals. High density metals, especially nickel, cobalt and chromium, have been the subject of extensive government toxicity studies. Notably, Christensen, H. E., ed., *Registry of Toxic Effects of Chemical Substances*, U.S. Department of Health, Education and Welfare, Rockville, Maryland (1975) has reported the toxicity of these metals and many of their salts. The HEW study reports, for example, a lethal dose 50 (LD50) of 26 mg/kg for the compound nickel chloride when injected intraperitoneally in the mouse. A lowest reported lethal dose (LDLo) of 10 mg/kg is reported for intravenous administration in a dog system. The LDLo is the lowest dose of a substance introduced by any route other than inhalation over any given period of time and reported to have caused death. A LD50 of 140 mg/kg is reported for copper(II)chloride (cupric chloride) when orally administered to the rat. A LD50 for intraperitoneal introduction to the mouse is recorded at 7400 micrograms per kilogram. The toxicity of cobalt(II)chloride is reported as a LD50 of 80 mg/kg (oral) and 20 mg/kg (intravenous) in the rat.

Additionally, in 1976, the National Cancer Institute, in its *Survey of Compounds Which Have Been Tested for Carcinogenic Activity*, reported cobalt chloride, copper, nickel and many of its salts, zinc and a number of its salts, lead, and other heavy metals as giving rise to animal tumors. Searle, C. D., *Chemical Carcinogens* ACS Monograph 193, Washington, American Chemical Society (1976) at pages 327–329 has specifically identified nickel as a particularly aggressive carcinogen.

Thus, in summary, certain amino acids and heavy metal salts have been used in attempts to improve the reaction of acetoacetic acid with sodium nitroprusside. Improvements have been realized through these efforts, however, these have been somewhat limited and, as can be readily seen, the use of many of these materials is accompanied by significant health hazards.

Also, it has been an accepted fact that use of the sodium nitroprusside test at alkaline pH (in contrast to acid pH) required a "two-dip" manufacturing procedure, this being a significant economic factor, in test strip production.

Further, there remain serious problems of instability, especially at alkaline pH, of aqueous nitroprusside solutions, slow and only moderately responsive reactivity, and instability of chromophoric species. Rapid degradation in color of resultant chromophoric species has lessened reliability after relatively short periods of time and has, therefore, required immediate reading by trained personnel.

OBJECTS OF THE INVENTION

It is therefore a principal object of the present invention to provide an improved test for detection of ketone bodies of the type using soluble nitroprusside.

It is another object of the invention to provide a ketone test means, such as a composition and device, using materials which are free of significant health hazards.

It is yet another object of the invention to provide ketone test means, of the type using nitroprusside, wherein the stability of the nitroprusside is maintained at both acid and alkaline pH.

It is therefore another object of the invention to provide a one-dip production method for ketone test devices intended for use at alkaline pH.

A further object of the present invention is to provide a ketone test means, including a composition and device, which facilitates the ionization of ketone bodies, thereby providing a shortened reaction time.

A still further object of the present invention is to provide a ketone test which is effective to maintain the stability of the resultant chromophoric complex.

Yet another object of the invention is to provide a ketone test composition having the above-mentioned advantages and in which the expense of manufacture is substantially reduced.

It is therefore another object of the invention to provide a ketone test composition and device wherein the above-mentioned advantages are provided by the presence of an inorganic salt of magnesium or calcium.

Additionally, it is an object of the invention to provide a ketone test composition and device wherein the advantage of even further stabilization of the resulting chromophoric complex is achieved by the synergistic combination of the above-mentioned metal salts with a primary amine.

Other objects and a fuller understanding of the invention will be had by referring to the following description and claims drawn to preferred embodiments thereof.

SUMMARY OF THE INVENTION

In accordance with the present invention there is provided test means for detection of ketone bodies in body fluids. More particularly, a composition is provided of the type having a nitroprusside salt wherein the improvement comprises addition of at least one inorganic salt of a metal selected from the group of magnesium and calcium. Optionally, at least one primary amine is combined therewith. The compositions are incorporated with a carrier, such as an absorbant matrix or a tablet, to provide a test device. The nitroprusside is stabilized in solution at alkaline pH by the metal salt, allowing for a single-dip production method, ionization of the ketone body is catalyzed by the metal salt, resulting in a shortened reaction time, and the resulting chromophoric complex is stabilized by the metal salt, resulting in prolonged reliability of color for reading. The chromophoric complex is further stabilized by the primary amine.

In a preferred embodiment, the composition comprises a soluble nitroprusside in combination with at least one inorganic salt such as $CaCl_2$ and, especially, $MgSO_4$. Other salts which can be used include $MgCl_2$, $MgBr_2$, $Mg(ClO_4)_2 \cdot 6H_2O$, $Mg(NO_3)_2 \cdot 2H_2O$, $Mg(NO_2)_2 \cdot 3H_2O$, $CaSO_4$, $Ca(BrO_3)_2 \cdot H_2O$, $Ca(ClO_3)_2$, $Ca(ClO)_2$ and $CA(HSO_3)_2$, for example. More than one metal salt can be included in the composition, the combination of $MgSO_4$ and $CaCl_2$ being especially preferred.

Preferred nitroprussides are the soluble nitroprusside salts. Such include alkali metal salts of nitroprusside like sodium or potassium nitroprusside.

The presence of these metal salts has been found to have a number of surprising effects. These include stabilization of soluble nitroprussides in aqueous solution at alkaline pH, facilitation of ketone body ionization, and stabilization of the resultant chromophoric species. Additionally, a single-step method using preparation solutions at alkaline pH is provided for producing devices intended for use at said alkaline pH.

These heretofore unrecognized properties and advantages are believed to result through the mechanism illustrated in Diagram A, although this is not a theory on which the present invention must be based.

Diagram A*

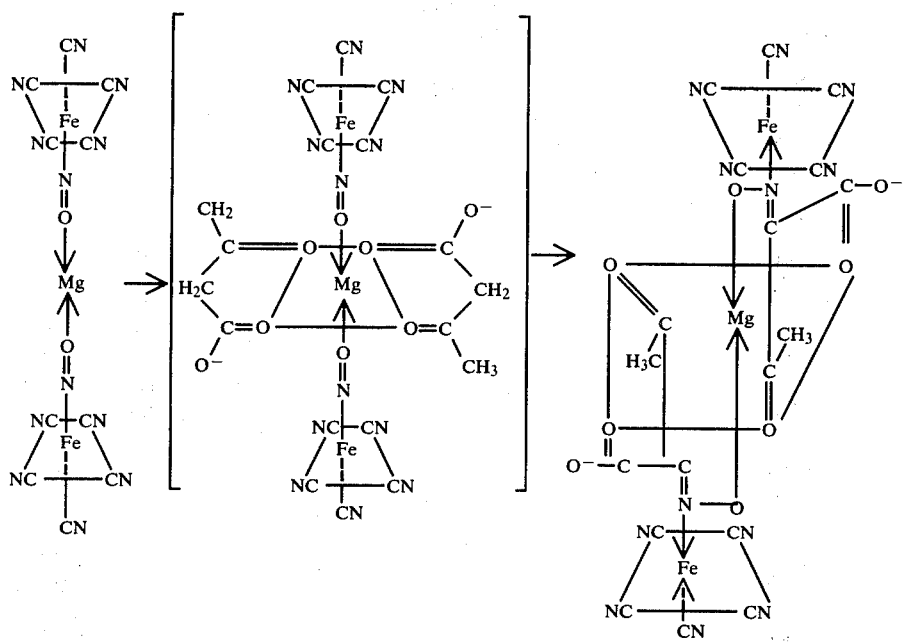

*The illustrations are in accordance with the nomenclature and illustrations in Cotton and Wilkinson, Advanced Inorganic Chemistry, John Wiley & Sons (1962).

Additionally, other advantageous properties, superior to those of tests heretofore available, have been demonstrated. These include enhanced stability under heat stress and humidity stress conditions, reduced differentiation time, sensitivity to ketone body concentrations lower than those previously detectable, a more intensely colored test, and significant economic advantages in the cost of materials used. Comparative cost quotations are set forth in the Chemical Marketing Reporter of Sept. 19, 1977 and support for each of the other advantageous properties is provided by the example, infra.

The metal salts used in the present invention are substantially free of toxicity or carinogenicity. For example, the lowest lethal dose reported in Christensen, supra, for magnesium sulfate (synonymous with Epsom Salts) is 750 mg/kg when injected intravenously in dog. Intraperitoneal and subcutaneous LDLo's in dog are more than double this amount. No LD50's are even reported for this compound. A single LD50 dose, of 2800 mg/kg, is reported for magnesium chloride when administered orally to rats. The reports for calcium chloride in rats includes a LD50 of 100 mg/kg (orally), a LDLo of 500 mg/kg (intraperitoneally) and 161 mg/kg (intravenously). These characteristics are in striking contrast to those of other metal salts, such as the metal salts previously discussed.

In another preferred embodiment, the composition further comprises at least one primary amine. One type of primary amine which is advantageously selected is exemplified by the amino acids. Others, which are preferred, are selected from the group of ethylene diamine, picolylamine, m-aminophenol and semicarbazide. Compounds selected from the group of aminomethanesulfonic acid, sulfanilic acid, cysteic acid, cyclohexylamine and pyridoxamine are also beneficially used. Combinations of such primary amines are likewise advantageously used, for example aminomethanesulfonic acid and pyridoxamine.

The addition of these primary amines has been discovered to demonstrate unexpected, beneficial properties. Among others, Schiff bases, formed of ketone bodies and a primary amine, have been discovered to act in synergistic combination with metal salts of this invention to form a highly sensitive ketone detection test with comparatively low amounts of constituents.

Optimum color development occurs when the protonated and free forms of the active amine are in equimolar concentration. Therefore, a primary amine is advantageously selected which has a pKa equal to the pH at which the test is to be conducted. The resultant blue color, and the chromphoric species producing it, is in contrast to the red color development resulting from the addition of the sodium nitroprusside and metal salt composition to a ketone body in the absence of a nitrogen source.

Thus, in addition to catalyzing the reaction of soluble nitroprusside with ketone bodies by addition of inorganic salts of magnesium or calcium, the promnastic effect of these metal salts on aldehyde and ketone moieties has now been advantageously applied to the field of nitroprusside tests by combining the metal salts with primary amines to form a metal complex, as shown in Diagram B below, in which two adjacent coordination sites of the metal are occupied by the carbonyl and the primary amine. This proximity of the two reactive species held in a rigid configuration about a metal ion, then, allows the metal ion to act as an electron reservoir and this facilitates their reaction to form the Schiff base with elimination of $H_2O$.

Diagram B

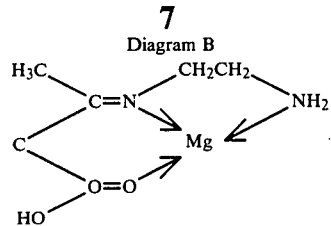

It is believed that the formation of a Schiff base between an amino acid, an amino acid analog or certain other primary amines and acetoacetic acid or acetoacetate undergoes the promnastic effect with a metal salt in a very rigid but most efficient bi-tridentate complex as illustrated in Diagram C.

Diagram C

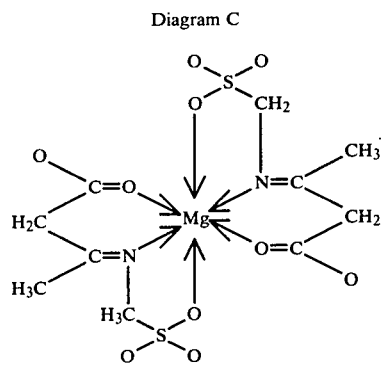

Also provided are test devices incorporating the compositions of the invention and a single-dip method of making such reagent test devices which comprises contacting a carrier, such as a matrix or tablet, with a nitroprusside in combination with an inorganic salt of magnesium or calcium, or the metal salt and a primary amine. When this contact is by impregnation with a solution of the composition according to the invention, the carrier so contacted is then dried. The solvent used in preparing solutions for the single-dip method may be water, physiological solutions, organic solvents or mixtures thereof.

The solution itself or a tablet containing the compositions according to the invention may be used to detect ketone bodies by adding it to a body fluid specimen such as urine, plasma or serum. Formation of the chromophoric complex with resultant color change is effected. However, the composition is advantageously used in the form of a solid preparation, rather than the solution itself.

Solid preparations, as described below, are preferably incorporated with a carrier matrix in strip format. The test device is advantageously used by momentarily dipping it in a test sample or by otherwise introducing a test sample into the carrier matrix, whereby a detectable color change results when ketone bodies are present. The test device may be used in the same way when samples of plasma, serum or other body fluids are tested. The test device of the invention may be mounted on an elongated support member, if desired.

The test device of the invention is sensitive to ketone bodies, particularly to acetoacetic acid and acetoacetate in the urine. Since characteristic color reaction takes place depending on the concentration of the ketone bodies to be detected, semi-quantitative detection for such ketone bodies is possible.

It is now possible by using the test composition and device of the invention to detect acetoacetic acid in urine in amounts at least as low as 1 milligram (mg)/deciliter (dl).

DESCRIPTION OF THE PREFERRED EMBODIMENTS

Although specific terms are used in the following description for the sake of clarity, these terms are intended to refer only to the particular embodiment of the invention selected for exemplary illustration, and are not intended to define or limit the scope of the invention.

Standard commercially available soluble nitroprussides, such as sodium nitroprusside are satisfactory for use. Likewise, metal salts and primary amines used in the invention are readily available commercial preparations. Magnesium and calcium inorganic salts are used in a range of from about 0.5 Molar (M) to about 2.0 M solutions. When primary amines, such as ethylene diamine, picolylamine, m-aminophenol, semicarbazinde, aminomethanesulfonic acid, sulfanilic acid, cysteic acid, cyclohexylamine and pyridoxamine, are combined with the metal salt they are present in the range of from about 1.0 to about 1.5% by weight concentrations. The combined materials can be introduced to the nitroprusside solution simultaneously or sequentially. Also, more than one calcium or magnesium metal salt or primary amine can be used concurrently.

Standard buffers such as Tris(hydroxymethyl)aminomethane [TRIS], piperazine-N,N'-bis(2-ethanesulfonic acid) [PIPES], N-tris-(hydroxymethyl)methyl-2-aminoethanesulfonic acid can be used.

The nitroprusside solution is maintained in a pH range of from about 7.0 to 9.2. The invention makes possible the stabilization of the nitroprusside in a generally alkaline pH range, which range provides improved nitroprusside reactivity.

The term carrier matrix can be envisioned to refer to bibulous and non-bibulous matrices which are insoluble in and maintain their structural integrity when exposed to water or physiological fluids. Suitable bibulous matrices which can be used include paper, cellulose, wood, synthetic resin fleeces, glass fiber, woven and non-woven fabrics and the like. Non-bibulous matrices include organo-plastic materials such as polystyrene, polypropylene or the like. When a bibulous matrix is employed, the matrix is advantageously affixed by suitable means, such as double-faced adhesive tape, to an insoluble support member, such as an organo-plastic strip, for ease of use.

Alternatively, the compositions of the invention may be embodied in a carrier taking the form of a pressed or molded tablet containing conventional carrier material.

Differentiation of 0 to 80 mg/dl refers to the time required for color formation sufficient to visually distinguish test devices exposed to 0 mg/dl, 20 mg/dl, 40 mg/dl and 80 mg/dl ketone concentrations.

A preferred method of preparing test devices according to the invention comprises incorporating, such as by impregnating, a carrier matrix with the composition of the present invention. In addition to impregnation, the devices of the present invention can be made by other suitable techniques such as printing or spraying the composition onto a substrate or matrix.

The process for using the devices comprises contacting a liquid sample with the device or test means and observing any resultant change in color of the device or of the sample as the case may be.

As contemplated by the invention, test means are provided which comprise a nitroprusside in combination with at least one inorganic salt of a metal selected from the group of magnesium and calcium, or the metal salt and a primary amine. The examples shown have been selected as merely illustrative and are not to be construed as a limitation of the invention. One skilled in the art will be able to make such variations, substitutions and changes in the ingredients and parameters as may seem desirable.

EXAMPLE I

The present experiment illustrates the stabilizing effect of $Mg^{++}$ on nitroprusside solutions.

Amounts of $MgSO_4.7H_2O$ (reagent grade) were dissolved up to concentrations of 1 M (Molar) and 2 M in 2 M tris-(hydroxymethyl)aminomethane [TRIS] aqueous buffer. Then, 2.5 grams of $Na_2[(NO)Fe(CN)_5]$ were added to 50 milliliters (ml) of the buffer solution. The pH was adjusted in aliquots of this solution, by dropwise addition of 0.1 M NaOH, to form the impregnation solutions indicated in Table 1.

TABLE 1

| pH | 2M $Mg^{++}$ | 1M $Mg^{++}$ |
|---|---|---|
| pH 9.2 | Mg 2(9.2) | Mg 1(9.2) |
| pH 9.0 | Mg 2(9.0) | Mg 1(9.0) |
| pH 8.6 | Mg 2(8.6) | Mg 1(8.6) |
| pH 8.3 | Mg 2(8.3) | Mg 1(8.3) |
| pH 8.0 | Mg 2(8.0) | Mg 1(8.0) |

Sheets of Whatman-3MM filter paper (Whatman, Inc., Clifton, N.J. 07014) 2.5 centimeters (cm) × 10 cm in size were respectively impregnated to saturation with solutions as shown in Table 1, dried at 125° Fahrenheit (F.), and cut to 0.5 cm × 0.5 cm to form devices the present invention. The devices so prepared were attached to plastic support members 0.5 cm × 8.0 cm using double-faced adhesive tape.

Devices impregnated with solutions which were freshly prepared, 3 hours old and 21 hours old, were tested by momentary immersion in urine solutions having 0, 20, 40 and 80 milligrams/deciliter (mg/dl) acetoacetic acid concentration and in a 2 g/dl aqueous ketone solution (stock ketone). Results obtained at the indicated reading time (in seconds) are reported in Table 2.

TABLE 2

| | Fresh solutions | |
|---|---|---|
| Test Device | 0-80 mg/dl Differentiation seconds (comments) | Stock Ketone (comment) |
| Mg 2(9.2) | 5 (excellent purple) | instant (deep purple) |
| Mg 2(9.0) | 10 (excellent) | instant (deep purple) |
| Mg 2(8.6) | 10 (good-pink/rose) | instant (purple) |
| Mg 2(8.3) | 10-20 (good-excellent) | instant (purple) |
| Mg 2(8.0) | 20-35 (good-excellent) | instant(purple) |
| Mg 1(9.0) | 15-25 (good-excellent) | instant (purple) |
| Mg 1(8.6) | 20-35 (good-excellent) | instant (purple) |
| Mg 1(8.3) | 25-40 (fair) | instant (purple) |
| Mg 1(8.0) | 35-40 (fair) | instant (purple) |
| | 3 Hour Solution | |
| Test Device | 0-80 mg/dl Differentiation seconds (comments) | Comparison with fresh solutions at 20 & 80 mg/dl |
| Mg 2(9.2) | 10 (excellent) | no significant difference |
| Mg 2(9.0) | 10-15 (good) | no significant difference |
| Mg 2(8.6) | 10-20 (good-very good) | no significant difference |
| Mg 2(8.3) | 20-25 (good) | no significant difference |
| Mg 2(8.0) | 15-20 (good) | no significant difference |
| Mg 1(9.2) | 15-20 (good) | no significant difference |
| Mg 1(9.0) | 15-20 (good-excellent) | no significant difference |
| Mg 1(8.6) | 20-35 (good-excellent) | no significant difference |
| Mg 1(8.3) | 25-40 (fair) | no significant difference |
| Mg 1(8.0) | 35-40 (fair) | no significant difference |
| | 21 Hour Solution | |
| Test Device | 0-80 mg/dl Differentiation seconds (comments) | Comparison with fresh solutions at 20 & 80 mg/dl |
| Mg 2(9.2) | 5-10 (very good) | no significant difference |
| Mg 2(9.0) | 10 (very good) | possibly a weaker reaction at 20 mg/dl after 21 hrs. |
| Mg 2(8.6) | 10-15 (very good) | no significant difference |
| Mg 2(8.3) | 15-20 (very good) | no significant difference |
| Mg 2(8.0) | 20 (very good) | possibly a weaker reaction at 80 mg/dl after 21 hrs. |
| Mg 1(9.2) | 15 (good) | possibly 21 hr. samples are more evenly developed |
| Mg 1(9.0) | 10-15 (good) | no significant difference |
| Mg 1(8.6) | 15-20 (good) | no significant difference |
| Mg 1(8.3) | 20-25 (good) | no significant difference |
| Mg 1(8.0) | 30 (good) | no significant difference |

The results obtained in this experiment demonstrate that the otherwise unstable nitroprusside solutions are rendered stable over prolonged periods by the addition of magnesium salts. The solutions, even when maintained for extended times, provided devices which readily detected ketone and differentiated between varying concentrations thereof.

EXAMPLE II

The use of pharmaceutical grade (U.S.P.) magnesium sulfate heptahydrate (Epsom Salts), available through over-the-counter distribution, instead of the reagent grade further illustrates that salts according to the present invention are generally recognized as safe.

Epsom salts (Walgreen Co., Dist., Deerfield, Ill.) was substituted for reagent grade $MgSO_4.7H_2O$ in, and a solution prepared according to, the following formulation:

| Epsom Salts | 49.5 g |
|---|---|
| $Na_2[(NO)Fe(CN)_5] . 2H_2O$ | 5.0 g |
| Distilled $H_2O$ | to 100.0 ml |

The 100 ml aqueous solution thus prepared was then adjusted to pH 9.2 with 1 N NaOH.

This red, clear solution was then used for single dip impregnation of 9 cm × 18 cm Eaton-Dikeman 204 (E&D) paper (Eaton-Dikeman, Mount Holly Springs, Pa. 17065). The paper was impregnated to saturation with the solution, dried at 50°-60° C. for 10 minutes and cut to 1 cm × 1 cm to form devices of the invention. The dried impregnated paper devices were then backed with double-faced adhesive tape, and fixed thereby to organo-plastic support members.

The devices so prepared were tested by momentarily immersing them in urine solutions of known ketone body concentration. Color development, in the expected shades of buff (negative) to reds (positives) differentiated between the presence of 0, 1, 10, 20, 40, and 80 mg/dl acetoacetic acid as quickly as the reagent grade formula (i.e., 5-10 seconds). The results demonstrated nitroprusside stabilization and reaction catalysis equal to that obtained with the use of reagent grade $MgSO_4$.

EXAMPLE III

A comparison, in device format, was made of Group IIa and IIIa metals as catalysts for reaction of $Na_2[(NO)Fe(CN)_5]$ with acetoacetic acid at a pH of 7.6.

Device impregnation solutions were prepared by dissolving compositions of the invention, having 2.5 g $Na_2[(NO)Fe(CN)_5]$ in combination with the formulations shown in Table 3, in 50 ml of TRIS aqueous buffer each.

TABLE 3

| COMPOUNDS | I | II | III | IV | V |
|---|---|---|---|---|---|
| $MgSO_4.7H_2O$ | 24.3 | — | — | — | — |
| $CaCl_2$ | — | 11.1g | — | — | — |
| $AlCl_3$ | — | — | 13.4g | — | — |
| $BaSO_4$ | — | — | — | 23.0g | — |
| $NaBF_4$ | — | — | — | — | 11.0g |

The pH of III could not be adjusted to 7.6 because of precipitation of the aluminum and the $BaSO_4$ of IV formed an insoluble emulsion.

Sheets of Whatman paper 2.5 cm × 10 cm in size were impregnated to saturation with the above-prepared solutions, dried at 125° F., and cut to 0.5 cm × 0.5 cm to form devices of the present invention. The devices so prepared were attached to plastic support members 0.5 × 8 cm using double-faced adhesive tape.

The devices were tested by momentary immersion in stock ketone and in urine solutions having 0, 20, 40, and 80 mg/dl acetoacetic acid concentrations with results as shown in Tables 4 and 5.

TABLE 4

| Control (no metal) | Stock Ketone | | | | |
|---|---|---|---|---|---|
| | I | II | III | IV | V |
| slight rose (5 min) | instant violet | instant red | unable to adjust pH | none (emulsion) | slight rose (slow) |

TABLE 5

| Compounds | 0-80 mg/dl Differentiation |
|---|---|
| I | Very good (10-15 seconds). violet color |
| II | Very good (30 seconds) |

TABLE 5-continued

| Compounds | 0-80 mg/dl Differentiation |
|---|---|
| | brick red color |

Thus, it is seen from Table 4 that of compounds I-V, only I ($MgSO_4$) and II ($CaCl_2$) provided effective test devices. Table 5 shows that devices prepared with compounds I and II readily distinguished between clinically significant ketone levels.

EXAMPLE IV

The compositions and devices of the present invention (C below) were compared to those using "heavy" metal salts as described in Example I of Ogawa, U.S. Pat. No. 3,880,590. Because the description of the exact formulation to be used is unclear, they were prepared according to two possible interpretations (A and B below).

(A) In this preparation, 30 ml of 0.3 M TRIS, having 5 grams per liter (g/l) $NiCl_2.6H_2O$ therein, were mixed with 9 milliliters (ml) of a solution consisting of:

| dimethylformamide | 5 g. |
|---|---|
| $Na_2[(NO)Fe(CN)_5].2H_2O$ (i.e., 95 g aqueous sodium nitroprusside) | 40 g. |
| distilled $H_2O$ | to 100 ml. |

The result of this mixing was a gray-blue emulsion which, when used to prepare devices according to the procedure set forth in Example II above, yielded a badly streaked device which reacted poorly when tested.

(B) In the alternate preparation, 30 ml of 0.3 M TRIS, having 5 g/l $NiCl_2.6H_2O$ therein, were mixed with 9 ml of a solution consisting of:

| dimethylformamide | 95 g. |
|---|---|
| $Na_2[(NO)Fe(CN)_5].2H_2O$ | 5 g. |
| distilled $H_2O$ | to 100 ml. |

This formulation provided a mint green translucent solution which was used to prepare devices. The devices were prepared exactly as in Example IV(A) above except that the paper was dried at room temperature in the dark.

(C) Test devices according to the invention were prepared exactly as in Example II above with the exception that reagent grade $MgSO_4.7H_2O$ was used in lieu of the pharmaceutical grade.

To present a fair comparison, preparation (B), the better of the two possible preparations (A) and (B) was used in comparative testing with the devices of the present invention. Each of the test devices so prepared was tested by momentary immersion in urine samples containing 0, 1, 10, 20, 40 and 80 mg/dl acetoacetic acid, respectively.

The nickel chloride test device (B) differentiated 0, 10, 20, 40 and 80 mg/dl acetoacetic acid in 30 seconds. The color range was off-white (negative) to a light lavender color at 80 mg/dl. Ketone concentrations of less than 10 mg/dl, but not as low as 1 mg/dl, were detected. The device according to the invention differentiated between 0, 1, 10, 20, 40 and 80 mg/dl acetoacetic acid in 5-10 seconds and detected ketone concentrations of 1 mg/dl. The color range was buff (negative) to a deep red color at 80 mg/dl.

Thus, it has been shown that devices prepared according to the invention are able to detect and differentiate lower concentrations of ketone than the prior art devices, and are able to do so more rapidly.

EXAMPLE V

In this experiment, a comparison was made of the effect of heat stress conditions on device performance when tested as in Example IV above.

The devices tested were prepared exactly as in Examples IV(B) and IV(C) above. Those used as controls were maintained at room temperature throughout the experiment. The remaining devices were subjected to dry heat of either 60° C. or 70° C. in a standard laboratory oven for varying periods as reported below.

After 3 days at 60° C., the device (C) of the present invention showed no difference from the control, whereas device (B), with $NiCl_2$, showed a slight lessening in color intensity.

After 7 days at 60° C., the device of the invention still showed no difference from the control, whereas the device containing $NiCl_2$ showed a definite 15-20 second lag time in color development by comparison with its control.

When maintained for 3 days at 70° C., device (C), using the $MgSO_4$ formulation, again showed no difference from the control whereas device (B), having the $NiCl_2$ formulation, demonstrated a 30 second lag time. Further, in device (B) all colors had dropped at least one whole color block in intensity. That is, for example, that the devices tested with 80, 40, 20 mg/dl, showed coloration corresponding to 40, 20, 10 mg/dl, respectively, in their controls.

Thus, this experiment demonstrates that devices according to the invention are substantially more heat stable than those of the prior art. Heat stress testing is generally recognized by those skilled in the art as indicative of product shelf-life.

EXAMPLE VI

In this experiment, a comparison was made of the effect of elevated humidity on various devices prepared exactly as in Examples IV(B) and IV(C) above. Devices used as controls were maintained under ambient humidity conditions throughout the experiment. The remaining devices were subjected to humidity stress conditions of 87% relative humidity at 28° C. for various periods of time.

The devices were tested, after humidity exposure, by momentary immersion in stock ketone and in urine solutions having 0, 20, 40, and 80 mg/dl acetoacetic acid concentrations. The results observed, after each duration of exposure, are reported below.

After one hour, device (C) prepared according to the invention showed absolutely no deviation from the control, while device (B) containing $NiCl_2$ showed a loss of ½ color block at each concentration of acetoacetic acid compared to its control.

After three hours, device (C) still showed no deviation from the control. Device (B) with $NiCl_2$, however, showed a loss of a full color block at each designated concentration.

Thus, the experiment demonstrates that devices prepared according to the invention are far superior to those utilizing prior art compositions under humidity stress conditions. This, again, is indicative of product stability.

EXAMPLE VII

The following experiment illustrates the catalyzing influence of an inorganic salt of magnesium on the $Na_2[(NO)Fe(CN)_5]$ reaction at higher pH.

A device impregnation solution was prepared from a 2 M aqueous TRIS solution by dissolving a composition, according to the invention, of 248 g/l $MgSO_4.7H_2O$ and 2.5 g/l of $Na[(NO)Fe(CN)_5]$ therein. Aliquots of the above solution were then adjusted to pH levels of 5.0, 6.0, 7.0, 8.0, 9.0, and 9.2 with 1 N NaOH or 1 N HCl as required.

Sheets of Whatman paper 2.5 cm × 10 cm in size were respectively impregnated to saturation with solutions as enumerated above, dried at 125° F., and cut to 0.5 cm × 0.5 cm to form devices of the present invention. The devices so prepared were attached to plastic support members 0.5 cm × 8 cm by double-faced adhesive tape.

The devices were tested by momentary immersion in stock ketone, as previously defined, and in urine solutions having 0, 20, 40, and 80 mg/dl acetoacetic acid concentrations, with the results shown in Table 6.

TABLE 6

| pH | 0-80 mg/dl Differentiation | Stock Ketone |
|---|---|---|
| 5.0 | none at 60 sec. | slow (pink-peach) |
| 6.0 | poor at 60 sec. | fast (rose) |
| 7.0 | fair at 15 sec. good at 45 sec. | faster (pink) |
| 8.0 | good at 15 sec. | instant (violet) |
| 9.0 | good at 15 sec. | instant (violet) |
| 9.2 | good at 15 sec. | instant (violet) |

Thus, contrary to previous tests undertaken at acid pH levels, the results obtained above show faster and more intense color development by an increase in pH up to highly alkaline levels when an inorganic magnesium salt catalyst is used.

EXAMPLE VIII

The following experiment demonstrates the synergistic action of epsom salts and aminomethanesulfonic acid in the detection of ketones.

TABLE 7

| Components | A | B | C | D |
|---|---|---|---|---|
| Epsom Salts | — | 49.5g | — | 49.5g |
| $Na_2[(NO)Fe(CN)_5] . 2H_2O$ | 5.0g | 5.0g | 5.0g | 5.0g |
| Aminomethanesulfonic acid | — | — | 1.5g | 1.5g |

Compositions prepared according to each of the formulations in Table 7 were dissolved in 100 ml of distilled $H_2O$, and the pH was adjusted to 7.3 with 0.1 M NaOH. It should be noted that pH 7.3 while slightly alkaline is also very near the pKa of the amine selected [pKa=6.5].

Sheets of E&D paper were respectively impregnated to saturation with the above-prepared solutions, dried at 50°-60° C. for 10 minutes and cut to 1 cm × 1 cm to form test devices. The devices were then backed with double-faced adhesive tape and fixed thereby to plastic support members.

Several minutes after dipping of the devices in urine containing acetoacetic acid, the device embodying component (A) showed no color development. However, the device embodying components (B) showed fair and the device embodying components (C) showed only a slight differentiation of 0 from 80 mg/dl acetoacetic acid (slight brick red color) in 30 sec. On the other hand, the device embodying components (D) demonstrated complete differentiation between 0, 20, 40 and 80 mg/dl acetoacetic acid in 30 seconds. Differentiation of 0 and 10 mg/dl appeared in 50–60 seconds. With the pH adjusted to 7.3, as expected, nitroferricyanide alone [as in (A)] did not develop color because the classical optimum pH environment is highly alkaline. While there was a slight catalytic effect at pH 7.3 by epsom salts (B) and by aminomethanesulfonic acid (C) individually, it is only when epsom salts and aminomethanesulfonic acid are used together (D) that one sees the greatly enhanced color development.

The experiment simply and clearly demonstrates synergism between epsom salts and a primary amine.

EXAMPLE IX

In the experiments described in this example, the stabilizing effect of combining a metal salt according to the invention and a primary amine was investigated.

Devices were prepared using sheets of Whatman paper 2.5 cm × 10 cm in size impregnated to saturation with a solution having the following formulation:

| | | |
|---|---|---|
| TRIS (2.0 Molar) | 50.0 ml | |
| $MgSO_4$ | 10.0 g. | |
| $NH_2CH_2SO_3H$ (AMSA) | 18.5 g. | (pH 7.236) |
| $Na_2[(NO)Fe(CN)_5]$ | 1.0 g. | |

The papers were dried at 52° C. for 15 minutes and cut into squares of 0.5 cm × 0.5 cm to provide devices of the present invention.

When the devices were tested with 1 drop of stock ketone, production of a bright purple was instantaneous. It is noteworthy that an effective test is provided even with reagent concentrations much lower than in Example VII.

The remaining impregnation solution of this Example was allowed to stand overnight in ambient air. Devices were then prepared therewith and tested as described herein. Differentiation of 0–80 mg/dl was observed in 10–13 seconds, with optimum development of the blue color at 30 seconds. Thus, the impregnating solution remained stable during this period.

Thus, this experiment has shown that the nitroprusside is stabilized at alkaline pH by using metal salts according to the invention in combination with a primary amine.

Then, 10 grams of $MgSO_4.7H_2O$ was added to approximately 90% of the impregnating solution, prepared above in this Example. Test devices were then prepared as above, but using this reformulated solution. On testing, the resulting devices exhibited initial color development that was discernable sooner, and provided differentiation of 0–80 mg/dl at a rate equal to that of the devices previously prepared from the impregnating solution without increased $Mg^{++}$.

Thus, a proportional relationship, characteristic of catalysis, is seen between the amount of magnesium salt present and the rate of color development.

EXAMPLE X

Solutions for use in the preparation of devices of the present invention are stabilized for even longer periods using the formulation shown below which includes the surfactant Steol CA-460 (Stepan Chemical Co., Northfield, Illinois 60094).

| | | |
|---|---|---|
| 1M aqueous TRIS | 50.0 ml | |
| $H_2NCH_2SO_3H$ | 1.17 g. | |
| Steol CA-460 | 0.5 g. | (pH 7.6) |
| $MgSO_4 . 7H_2O$ | 15.0 g. | |
| $Na_2[(NO)Fe(CN)_5]$ | 3.0 g. | |

When devices impregnated with a solution having this formulation, and prepared as in Example IX, were tested, rapid stock ketone reaction was observed (red-rose color) and 0–80 mg/dl differentiation occurred in 20–30 seconds with 0 mg/dl and 80 mg/dl being distinguishable after 5 seconds.

The formulation shown above was changed by the addition of 6 g. of $MgSO_4.7H_2O$ to the solution (pH is 7.75) and devices were prepared as before. After one week, this solution containing the increased $MgSO_4.7H_2O$ was used to prepare devices as above. When tested, these devices gave instant rose color with ketone stock, and 0–80 mg/dl differentiation in 15 seconds or less. The solution had been stored under ambient conditions.

The results reported above demonstrate the further stabilization, as compared to the previous example, which is obtained by addition of surface-active materials.

EXAMPLE XI

The following experiment was performed to determine the effect of combinations of $Mg^{++}$ and various other primary amines.

Solutions were prepared following the formulations of Table 8 in which 2 M aqueous TRIS solution containing 20 g/l Steol CA 460 and 120.4 g/l $MgSO_4.7H_2O$ (TRIS solution) is combined respectively with various primary amines. These solutions were respectively impregnated into Whatman paper to form devices as in Example IX.

TABLE 8

| Formulations | | pH 7.6 (High) | pH 6.0 (Low) |
|---|---|---|---|
| TRIS solution | 50.0 ml | | |
| Histadine | 2.1 g. | M1H* | M1L |
| $Na_2[(NO)Fe(CN)_5]$ | 2.5 g. | | |
| TRIS solution | 50.0 ml | | |
| Glycine | 0.75 g. | M2H | M2L |
| $Na_2(NO)Fe(CN)_5$ | 2.5 g. | | |
| TRIS solution | 50.0 ml | | |
| AMSA | 1.11 g. | M3H | M3L |
| $Na_2[(NO)Fe(CN)_5]$ | 2.5 g. | | |
| TRIS solution | 50.0 ml | | |
| Cysteic acid | 1.87 g. | M4H | M4L |
| $Na_2[(NO)Fe(CN)_5]$ | 2.5 g. | | |
| TRIS solution | 50.0 ml | | |
| Picolylamine | 1.08 g. | M5H | M5L |
| $Na_2[(NO)Fe(CN)_5]$ | 2.5 g. | | |

*Characters indicate metal used (M = magnesium) number of formulation (1–5), and pH level (H = high; L = low).

The devices were tested by momentary immersion in stock ketone and in urine solutions having 0, 20, 40, and 80 mg/dl ketone with results as shown in Table 9.

TABLE 9

| # | 0–80 mg/dl Differentiation seconds (comments) | Stock Ketone (comment) |
|---|---|---|
| M1H | 15 (good) | instant (violet) |
| M1L | 90 (weak) | slow (med. |

TABLE 9-continued

| # | 0-80 mg/dl Differentiation seconds (comments) | Stock Ketone (comment) |
|---|---|---|
| | | pink) |
| M2H | 15-20 (good) | instant (violet) |
| M2L | 90-120 (weak) | slow (pink-blue) |
| M3H | 15-20 (good) | instant (violet) |
| M3L | 90-120 (weak) | slow (pink-blue) |
| M4H | 20 (good) | instant (violet) |
| M4L | 60 (fair) | moderate |
| M5H | 30 (fair) | moderate (violet) |
| M5L | 60 (fair) | slow (pink) |

Thus, the reported results indicate that a wide variety of primary amines, both aromatic and aliphatic, are effective in combination with magnesium salts of the invention. Also, it is evident that elevation of pH is an important factor.

EXAMPLE XII

The following experiment illustrates the combined effect of $Ca^{++}$ and primary amines.

Solutions were prepared following the formulations of Table 10 in which 2 M aqueous TRIS solution containing 20 g/l Steol CA 460 and 111 g/l $CaCl_2$ (TRIS Solution) is combined respectively with various primary amines.

TABLE 10

| Formulation | | pH 7.6 (High) | pH 6.0 (Low) |
|---|---|---|---|
| TRIS solutin | 50.0 ml | | |
| Histidine . HCl . $H_2O$ | 2.1 g. | C1H | C1L |
| $Na_2[(NO)Fe(CN)_5]$ | 2.5 g. | | |
| TRIS solution | 50.0 ml | | |
| Glycine | 0.75 g. | C2H | C2L |
| $Na_2[(NO)Fe(CN)_5]$ | 2.5 g. | | |
| TRIS solution | 50.0 ml | | |
| AMSA | 1.11 g. | C3H | C3L |
| $Na_2[(NO)Fe(CN)_5]$ | 2.55 g. | | |
| TRIS solution | 50.0 ml | | |
| Cysteic Acid | 1.87 g. | C4H | C4L |
| $Na_2[(NO)Fe(CN)_5]$ | 2.5 g. | | |
| TRIS solution | 50.0 ml | | |
| Picolylamine | 1.08 g. | C5H | C5L |
| $Na_2[(NO)Fe(CN)_5]$ | 2.5 g. | | |

Sheets of Whatman paper 2.5 cm × 10 cm in size were respectively impregnated to saturation with each of the above-prepared solutions, dried at 125° F., and cut to 0.5 cm × 0.5 cm to form devices of the present invention. The devices so prepared were attached to plastic support members 0.5 cm × 8.0 cm by double-faced adhesive tape.

The devices were tested by momentary immersion in stock ketone and in urine solutions having 0, 20, 40, and 80 mg/dl ketone, with results as shown in Table 11.

TABLE 11

| # | 0-80 mg/dl Differentiation seconds (comments) | Stock Ketone (comment) |
|---|---|---|
| C1H | 30-60 (good-excellent) | instant (rose-violet) |
| C1L | 60 (weak blue) | slow (violet) |
| C2H | 45-90 (good-excellent) | instant (rose-violet) |
| C2L | 90 (weak) | slow (violet-pink) |
| C3H | 60-90 (good) | instant (rose-blue) |
| C3L | 120 (weak) | slow (pink) |
| C4H | 60-90 (weak-fair) | instant (rose) |
| C4L | 60-120 (weak-fair) | slow (pink-violet) |
| C5H | 30-60 (fair-good) | instant (rose) |
| C5L | 60 (weak) | slow (pink-violet) |

It can be seen that a wide variety of primary amines are effectively combined with calcium salts as well. Elevated pH is also shown to be an important factor.

Although the invention has been described with a certain degree of particularity, it is understood that the present disclosure has been made only by way of example and that numerous changes in the details may be resorted to without departing from the scope of the invention.

What is claimed is:

1. A test composition for detection of ketones at alkaline pH which comprises a soluble nitroprusside in combination with a compound to produce said alkaline pH and at least one inorganic salt of a metal selected from the group consisting of magnesium and calcium.

2. The test composition of claim 1 wherein the metal salt is selected from the group consisting of $MgSO_4$ and $CaCl_2$.

3. The test composition of claim 1 wherein there is present a combination of metal salts.

4. The test composition of claim 3 wherein said combination comprises $MgSO_4$ and $CaCl_2$.

5. The test composition of claim 1 wherein said nitroprusside is sodium nitroprusside.

6. A ketone detection device which comprises a carrier matrix and, incorporated therewith, the test composition of claim 1.

7. The device of claim 6 in which the carrier matrix is bibulous.

8. A ketone detection device which comprises a tablet incorporated with the test composition of claim 1.

9. A ketone detection device which comprises a carrier matrix incorporated with a composition comprising sodium nitroprusside, $MgSO_4$ and a component to produce an alkaline pH.

10. A process for the preparation of a ketone test device which comprises incorporating a carrier matrix with the test composition of claim 1.

11. The process of claim 10 wherein said incorporating is impregnating with a solution of said test composition, followed by drying.

12. A process for detection of ketone in a liquid sample which comprises contacting said sample with the test composition of claim 1 and observing any resultant color formed.

13. A process for detection of ketone in a liquid sample which comprises contacting said sample with the device of claim 6 and observing any resultant color formed.

14. A test composition for the detection of ketones at an alkaline pH which comprises a soluble nitroprusside, a component to produce said alkaline pH, at least one inorganic salt of a metal selected from the group consisting of magnesium and calcium and at least one primary amine.

15. The test composition of claim 14 wherein the at least one metal salt is selected from the group consisting of $MgSO_4$ and $CaCl_2$.

16. The test composition of claim 14 wherein the at least one metal salt is $MgSO_4$.

17. The test composition of claim 14 wherein the at least one metal salt comprises the combination of $MgSO_4$ and $CaCl_2$.

18. The test composition of claim 14 wherein the primary amine is selected from those having a pKa approximately the same as the pH at which the test means is to be used.

19. The test composition of claim 14 wherein the primary amine is aminomethanesulfonic acid, sulfanilic acid, cysteic acid, cyclohexamine, pyridoxamine, ethylene diamine, picolylamine, m-aminophenol or semicarbazide.

20. The test composition of claim 19 wherein the primary amine is aminomethanesulfonic acid.

21. The test composition of claim 14 wherein the nitroprusside is sodium nitroprusside.

22. A ketone detection device which comprises a carrier matrix and, incorporated therewith, the test composition of claim 14.

23. A process for the preparation of a ketone test device which comprises incorporating a carrier matrix with the test composition of claim 14.

24. A process for detection of ketone in a liquid sample which comprises contacting said sample with the test composition of claim 14 and observing any resultant color formed.

25. A process for detection of ketone in a liquid sample which comprises contacting said sample with the device of claim 22 and observing any resultant color formed.

* * * * *

UNITED STATES PATENT AND TRADEMARK OFFICE
CERTIFICATE OF CORRECTION

PATENT NO. : 4,147,514

DATED : April 3, 1979

INVENTOR(S) : Thomas A. Magers, David L. Tabb

It is certified that error appears in the above–identified patent and that said Letters Patent are hereby corrected as shown below:

Column 7, Diagram B, the formula which now reads

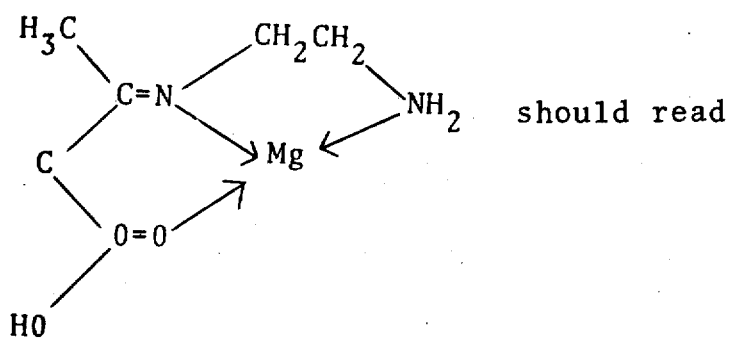 should read 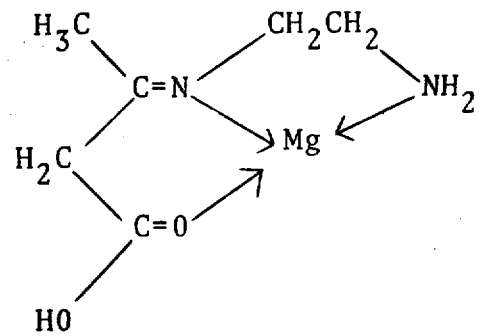

Signed and Sealed this

Twentieth Day of November 1979

[SEAL]

Attest:

RUTH C. MASON
*Attesting Officer*

LUTRELLE F. PARKER
*Acting Commissioner of Patents and Trademarks*

UNITED STATES PATENT AND TRADEMARK OFFICE
CERTIFICATE OF CORRECTION

PATENT NO. : 4,147,514

DATED : April 3, 1979

INVENTOR(S) : Thomas A. Magers, David L. Tabb

It is certified that error appears in the above-identified patent and that said Letters Patent are hereby corrected as shown below:

Column 7, Diagram C, the formula which now reads

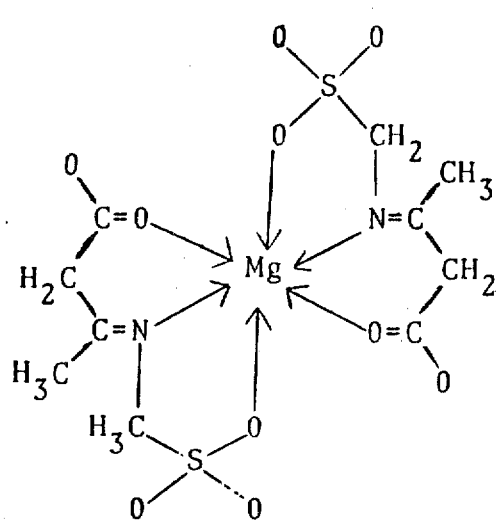     should read     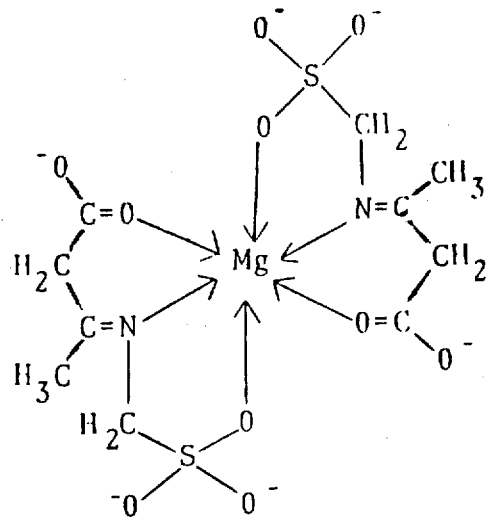

Column 17, Table 10, the portion reading "solutin" should read --solution--.